United States Patent
Varner et al.

(10) Patent No.: US 10,695,511 B2
(45) Date of Patent: Jun. 30, 2020

(54) METHOD FOR CALIBRATING PERFORMANCE RANGE OF A PNEUMATICALLY SEALED TROCAR

(71) Applicant: Conmed Corporation, Utica, NY (US)

(72) Inventors: Kenneth Varner, New Haven, CT (US); Mikiya Silver, New Haven, CT (US)

(73) Assignee: Conmed Corporation, Utica, NY (US)

( * ) Notice: Subject to any disclaimer, the term of this patent is extended or adjusted under 35 U.S.C. 154(b) by 191 days.

(21) Appl. No.: 15/972,405

(22) Filed: May 7, 2018

(65) Prior Publication Data

US 2019/0070369 A1 Mar. 7, 2019

Related U.S. Application Data

(60) Provisional application No. 62/555,236, filed on Sep. 7, 2017.

(51) Int. Cl.
| | |
|---|---|
| *A61M 13/00* | (2006.01) |
| *A61B 17/34* | (2006.01) |
| *G16H 40/60* | (2018.01) |
| *G16H 40/40* | (2018.01) |
| *A61B 17/00* | (2006.01) |
| *A61B 90/00* | (2016.01) |

(52) U.S. Cl.
CPC ....... *A61M 13/003* (2013.01); *A61B 17/3474* (2013.01); *G16H 40/40* (2018.01); *G16H 40/60* (2018.01); *A61B 2017/00022* (2013.01); *A61B 2017/00544* (2013.01); *A61B 2017/00725* (2013.01); *A61B 2090/032* (2016.02); *A61M 2205/3344* (2013.01); *A61M 2205/50* (2013.01); *A61M 2205/702* (2013.01)

(58) Field of Classification Search
CPC ........ A61M 2205/3344; A61M 13/003; A61M 2210/1021; A61M 13/00
See application file for complete search history.

(56) References Cited

U.S. PATENT DOCUMENTS

| | | | |
|---|---|---|---|
| 5,800,383 A | 9/1998 | Chandler et al. | |
| 7,854,724 B2 | 12/2010 | Stearns et al. | |
| 8,715,219 B2 | 5/2014 | Stearns et al. | |
| 8,795,223 B2 | 8/2014 | Stearns et al. | |

(Continued)

FOREIGN PATENT DOCUMENTS

JP H05-154092 A 6/1993

OTHER PUBLICATIONS

International Search Report issued in corresponding PCT Patent Application No. PCT/US2018/049387, dated Jan. 7, 2019.

*Primary Examiner* — Emily L Schmidt
(74) *Attorney, Agent, or Firm* — Locke Lord LLP; Scott D. Wofsy (57) ABSTRACT

A method and assembly for calibrating the pneumatic performance range of a system for delivering pneumatic power to a trocar, which includes the steps of: supplying pneumatic power to a trocar to achieve a desired cavity pressure; measuring the pneumatic power and cavity pressure over a time period, as the system attempts to maintain the desired cavity pressure; calculating performance characteristics of the trocar based on the measured cavity pressure and pneumatic power values; and adjusting the pneumatic power supplied to the trocar based upon the performance characteristics of the trocar.

8 Claims, 6 Drawing Sheets

(56) References Cited

U.S. PATENT DOCUMENTS

| | | |
|---|---|---|
| 8,961,451 B2 | 2/2015 | Stearns et al. |
| 9,295,490 B2 | 3/2016 | Stearns et al. |
| 2005/0222491 A1 | 10/2005 | Noda et al. |
| 2006/0129087 A1* | 6/2006 | Uesugi ............... A61M 13/003 604/26 |
| 2011/0125084 A1 | 5/2011 | Stearns et al. |
| 2016/0346454 A1 | 12/2016 | Woolford |

* cited by examiner

METHOD FOR CALIBRATING PERFORMANCE RANGE OF A PNEUMATICALLY SEALED TROCAR

CROSS-REFERENCE TO RELATED APPLICATION

This application claims the benefit of priority from U.S. Provisional Patent Application Ser. No. 62/555,236, filed Sep. 7, 2017, the disclosure of which is incorporated herein by reference in its entirety.

BACKGROUND OF THE INVENTION

1. Field of the Invention

The subject disclosure relates to gas delivery systems for use with surgical access devices, and more particularly, to a method for calibrating the performance range of a system for delivering pneumatic power to a pneumatically sealed trocar.

2. Description of Related Art

When operating a pneumatically sealed trocar such as the type of devices disclosed, for example, in commonly assigned U.S. Pat. Nos. 7,854,724 and 8,795,223, by way of an electro-mechanical control system such as the type of systems disclosed, for example, in commonly assigned U.S. Pat. Nos. 8,715,219; 8,961,451; and 9,295,490, it may be advantageous to calibrate the performance range of the control system to the specific performance characteristics of the trocar, for a number of reasons.

For example, calibrating an electro-mechanical control system to supply a specific range of pneumatic power can improve safety by designating limits to prevent the system from undersupplying or oversupplying pneumatic power to a pneumatically sealed trocar. Furthermore, calibration can improve system efficiency by ensuring the electro-mechanical control system stays within a designated range and preventing inefficient over-powering or under-powering of the system. Finally, calibration allows for more precise device control, which can lead to further product development or product line extensions, by allowing the device to behave adequately for any type of pneumatically sealed trocar or other end effector. This enables a simpler product development process, by ensuring the system will calibrate to any trocar or other product that is created.

Design differences can cause variations in the pneumatic power requirements or characteristics of different pneumatically sealed trocars. This can be impacted by manufacturing variability, differences in the cross-sectional area of the seal region (i.e., 5 mm vs. 12 mm), as well as varied efficiency, flow resistance, design and resistance of associated parts of the system such as tube sets and insufflation device interfaces, and other operational and environmental factors such as elevation and humidity. Furthermore, different pneumatically sealed trocars may exhibit behaviors that vary depending on the operating range. Just as a car/engine can be more fuel efficient at different speeds, a pneumatically sealed trocar can have different sensitivity when powered at a low range versus a high range.

A typical calibration process involves a system of controls and sensors in which one outcome (or a desired outcome) is held steady, while measurements of a certain metric of the system are observed and recorded. Then, the system can be adjusted (based on some known entity) to operate properly.

For example, a pressure gauge can be calibrated through the following method. First, the pressure gauge is connected to a closed vessel and a known pressure (e.g., 5 psi) is applied to the closed vessel through a secondary device. Then, the measured pressure in the vessel is read on the pressure gauge, and the difference between the known applied pressure and the measured pressure reading is noted. Thereafter, the pressure gauge can be adjusted so that the reading of the pressure gauge matches the known pressure value. In this case, there is one set of measurements taken and the known outcome is controlled.

It would beneficial to translate this type of calibration process to a pneumatically sealed trocar with an electro-mechanical control system, as identified above, where one might expect the system to target a certain output (e.g., an abdominal pressure of 15 mmHg) and then measure the pneumatic power that is required to achieve that output with a specific trocar. Those skilled in the art will readily appreciate that a calibration process could be based on those pneumatic power measurements.

Furthermore, it would be beneficial to create a calibration process for a pneumatically sealed trocar with an electro-mechanical control system, as identified above, where one might expect the system to target a certain output (e.g., an abdominal pressure of 15 mmHg) and then measure both the output of the system and the pneumatic power that is controlled to achieve that output with a specific trocar. Those skilled in the art will readily appreciate the use of loop controllers in combination with embedded electro-mechanical control systems, as identified above. Closed-Loop controllers use sensors that feedback into electro-mechanical components that are then adjusted to achieve a certain output.

A closed-loop controller is designed to maintain a target even in the presence of disturbances to the system (e.g., leakages from the surgical cavity or externally-applied over-pressures such as when a surgeon presses on the cavity). In order for the controller to be successful, the system must be able to vary the input to maintain a target output. Those skilled in the art will readily appreciate that a calibration process could be based on both pneumatic power measurements and the output abdominal pressure measurements, and the subject invention is directed to such a method of calibration.

SUMMARY OF THE DISCLOSURE

The subject invention is directed to a new and useful method of calibrating the pneumatic performance range of a system for delivering pneumatic power to a trocar. The method includes the steps of: supplying pneumatic power to a trocar to achieve a desired cavity pressure; measuring the pneumatic power and cavity pressure over a time period, as the system attempts to maintain the desired cavity pressure; calculating performance characteristics of the trocar based on the measured cavity pressure and pneumatic power values; and adjusting the pneumatic power supplied to the trocar based upon the performance characteristics of the trocar.

In one embodiment of the invention, the method further includes the step of determining an average pneumatic power value and an average cavity pressure value for the time period for calculating the performance characteristics of the trocar. In another embodiment of the invention, the method includes the step of determining a filtered pneumatic power value and a filtered cavity pressure value for the time period for calculating the performance characteristics of the trocar. The step of determining a filtered pneumatic power value and a filtered cavity pressure value involves a processing methodology selected from the group consisting of a weighted average, a moving average, a curve-fitting, an additive smoothing, Butterworth filtering, digital filtering, exponential smoothing and low-pass filtering.

Preferably, the step of calculating performance characteristics of the trocar involves reference to a look-up table or a scale with known values. The method further includes the step of setting operating limits around the calculated performance characteristics of the trocar, relating to the pneumatic power that can be supplied to the trocar.

The subject invention is also directed to a method of calibrating the pneumatic performance range of a system for delivering pneumatic power to a trocar, which includes the steps of: supplying pneumatic power to a trocar to achieve a desired cavity pressure at a plurality of different output levels; measuring the pneumatic power and cavity pressure over a time period at each output level, as the system attempts to maintain the desired cavity pressure at each output level; calculating performance characteristics of the trocar based on the measured cavity pressure and pneumatic power values at each output level; and adjusting the pneumatic power supplied to the trocar based upon the performance characteristics of the trocar.

In this embodiment of the invention, the method further includes the step of determining an average pneumatic power value and an average cavity pressure value for the time period at each output level for calculating the performance characteristics of the trocar. In another embodiment of the invention, the method includes the step of determining a filtered pneumatic power value and a filtered cavity pressure value for the time period at each output level for calculating the performance characteristics of the trocar. Preferably, the step of calculating performance characteristics of the trocar involves reference to a look-up table or a scale with known values. The method also includes the step of setting operating limits around the calculated performance characteristics of the trocar, relating to the pneumatic power that can be supplied to the trocar.

These and other features of the calibration method of the subject invention and the way in which it is employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art will readily understand how to use the calibration process of the subject invention without undue experimentation, preferred embodiments thereof will be described in detail herein below with reference to the figures wherein.

DETAILED DESCRIPTION OF THE PREFERRED EMBODIMENTS

In the detailed description that follows, a unique calibration method is described which involves a pneumatically sealed trocar such as the type of trocar that is disclosed in commonly assigned U.S. Pat. Nos. 7,854,724 and 8,795,223, and an electro-mechanical control system such as the type of system that is disclosed in commonly assigned U.S. Pat. Nos. 8,715,219; 8,961,451; and 9,295,490. Each of these commonly assigned patents is hereby incorporated by reference into the subject application in their entirety for purposes of enablement.

Figure 1:
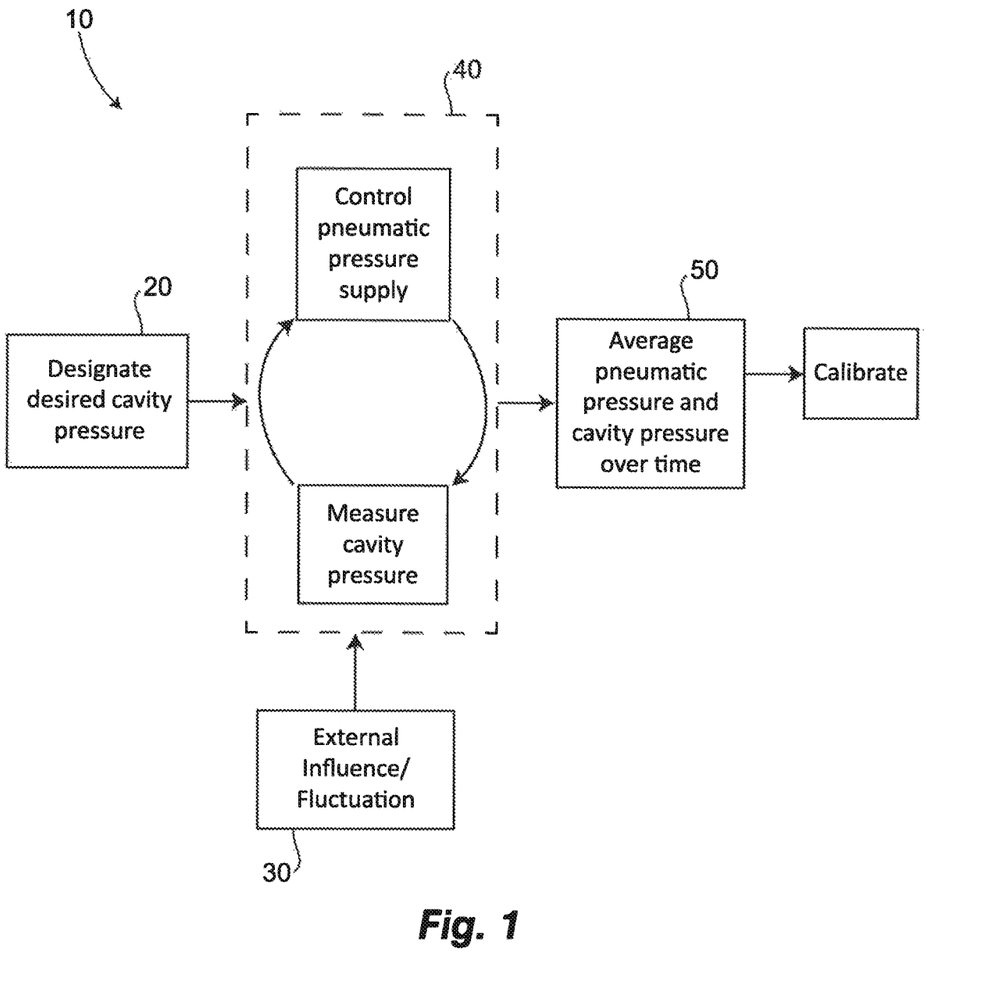
FIG. 1 is a process flow diagram illustrating the novel calibration method of the subject invention.

Referring now to FIG. 1, in general the novel calibration method 10 of the subject invention involves an operating environment that includes a device, such as a closed-loop controller, that controls the pneumatic power supplied to a trocar to achieve a desired outcome (i.e., abdominal cavity pressure) as described at process block 20, and wherein external influences and fluctuating cavity pressure results in an "unsteady" state or deviations, as described at process block 30. Fluctuations or disturbances in cavity pressure can result from leakages or externally applied over-pressure from surgical instruments or operating room staff.

At step 40, the device measures pneumatic power supplied to the trocar (pneumatic supply pressure) and abdominal cavity pressure over a predetermined period of time (e.g., over a few or several seconds). Then, at step 50, in accordance with one embodiment of the invention, average pneumatic power and average cavity pressure values are used to define trocar characteristics at the measured outcome cavity pressure. It should be understood that the data can be processed or filtered in ways other than averaging. Thereafter, at step 60, calibration of the system is achieved by adjusting the pneumatic power supplied to the trocar from the measured outcome value to the target outcome value.

The novel method of the subject invention does not look at just the one controlled outcome (i.e., 15 mmHg as in the above example), but rather it looks at a set of outcome measurements that approximate a system-controlled target outcome. When a dynamic system is subjected to outside influences (for example, if the volume of the closed vessel were to be dynamically altered) it creates instability in the system. Whereas, in the pressure gauge example described above, a known static value can be applied to the closed vessel and held for a set period of time for calibration. In a surgical scenario this can be a complex task. In this case, patient movement (e.g., muscle contractions and breathing), surgeon/nurse influence (e.g., pressing on the abdominal cavity), passing of surgical instruments through the trocar, smoke evacuation and other external influences can cause the system to be unstable.

For example, a target abdominal pressure of 15 mmHg might fluctuate between 12-18 mmHg due to these external influences. As such, calibrating pneumatic power performance to the target value may yield a skewed or inaccurate result. This effect is exacerbated when the system being calibrated is in and of itself dynamic, such as with an embedded control system with feedback loops.

Instead of looking at just one static known value (e.g., 5 psi or 15 mmHg), by considering a dynamic output value, a more accurate calibration can be achieved for the system. For example, if the abdominal pressure is varying between 12-18 mmHg, but is skewed more to the low end of that range, it might be better to calibrate the pneumatic power of the system to 14 mmHg instead of 15 mmHg.

Data processing for this calibrating method can be done in a number of different ways accepted across a range of industries and applications. In one embodiment of the invention, a simple average over a time period can be used to calibrate the system to its true output. Alternative processing methodologies can be employed in the subject invention, including, for example, a weighted and/or moving average, a curve-fitting, an additive smoothing, Butterworth filtering, digital filtering, exponential smoothing, low-pass filtering, or other filtering methods known in the art can be used to determine the best output for calibrating the system.

The choice of data processing methodology may be influenced by the measurement tools or sensors in the system. For example, if a slowly-sampling sensor is used, outliers may over-influence the result, so values within two standard deviations may be weighted more than data outside that range.

In one embodiment of this proposed method, the average driving pressure (pneumatic power) and average abdominal cavity pressure (output) are recorded over some period of time, as the system's embedded control features attempt to maintain a target abdominal pressure. The average pneumatic power values would then be used to define the trocar performance characteristics at the average abdominal pressure value. Then, the system will calculate the expected baseline performance characteristic at the target output.

For example, if the average pneumatic power is 50 psi, and the average abdominal pressure was 14 mmHg, then the expected baseline performance of that trocar at 15 mmHg might be 55 psi calculation could be based on some known look-up table or a sliding scale. Then, operating bounds would be set or calculated around the calculated baseline performance characteristics of the trocar, to set low and high limits on the pneumatic power that can be supplied to the trocar.

To further illustrate the benefits and advantages provided by the calibration process of the subject invention over the prior art, reference will be made to FIGS. 2-6, which provide graphical representations of different calibration processes, including several typical prior art calibration methods.

Figure 2:
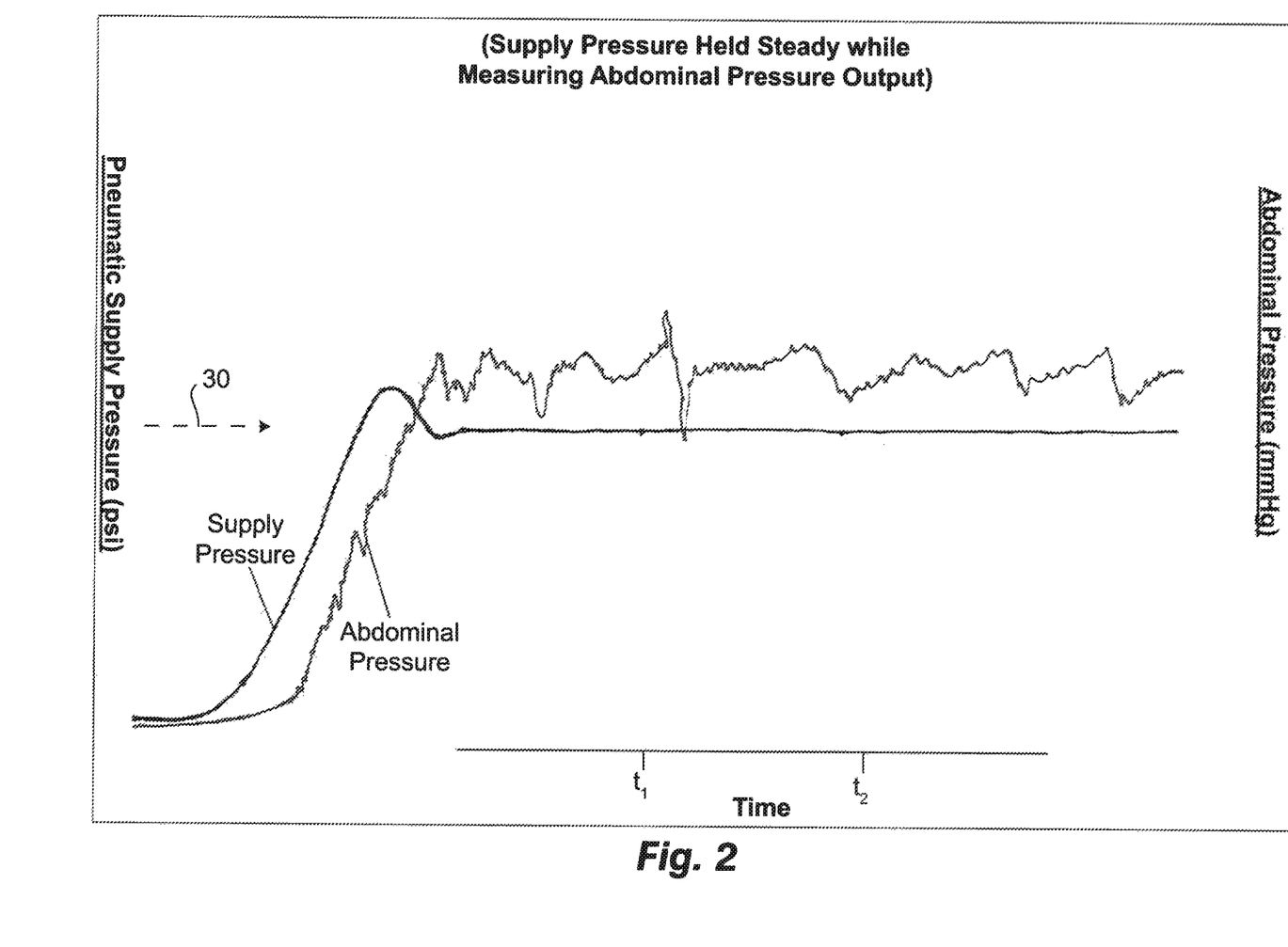
FIG. 2 is a graphical illustration of a typical simple calibration method wherein pneumatic supply pressure is held steady while abdominal cavity pressure output is measured.

Referring first to FIG. 2, there is illustrated a graphical representation of a typical prior art calibration process. Here, the system holds the supply pressure (pneumatic power) constant and measures the output (abdominal pressure). For example, the control software might hold supply pressure steady at 30 psi and measure the resultant abdominal pressure over time. In FIG. 2, the dashed arrow designated by reference numeral 30 represents the level of pneumatic power that the system provides and holds steady during the calibration process.

Using this basic method, a calibration could happen at a single time point. For example, the abdominal pressure can be measured at that time $t_1$. However, the process is susceptible to external influences or disturbances such as a leakage or an over-pressure condition from someone pushing against the abdomen, which can impact the calibration. Therefore, a better method would be to take an average (e.g., a straight average or filtered average) of the abdominal pressure over a time period.

For example, an average can be taken over the period of time extending from $t_1$ to $t_2$, to reduce the risk of an inaccurate calibration due to disturbances. While this method benefits from its simplicity, there is a disadvantage to its use, because abdominal pressure is not being controlled during the calibration process. Therefore, different trocars will result in different abdominal pressures, which would yield an unsatisfactory clinical result.

Figure 3:
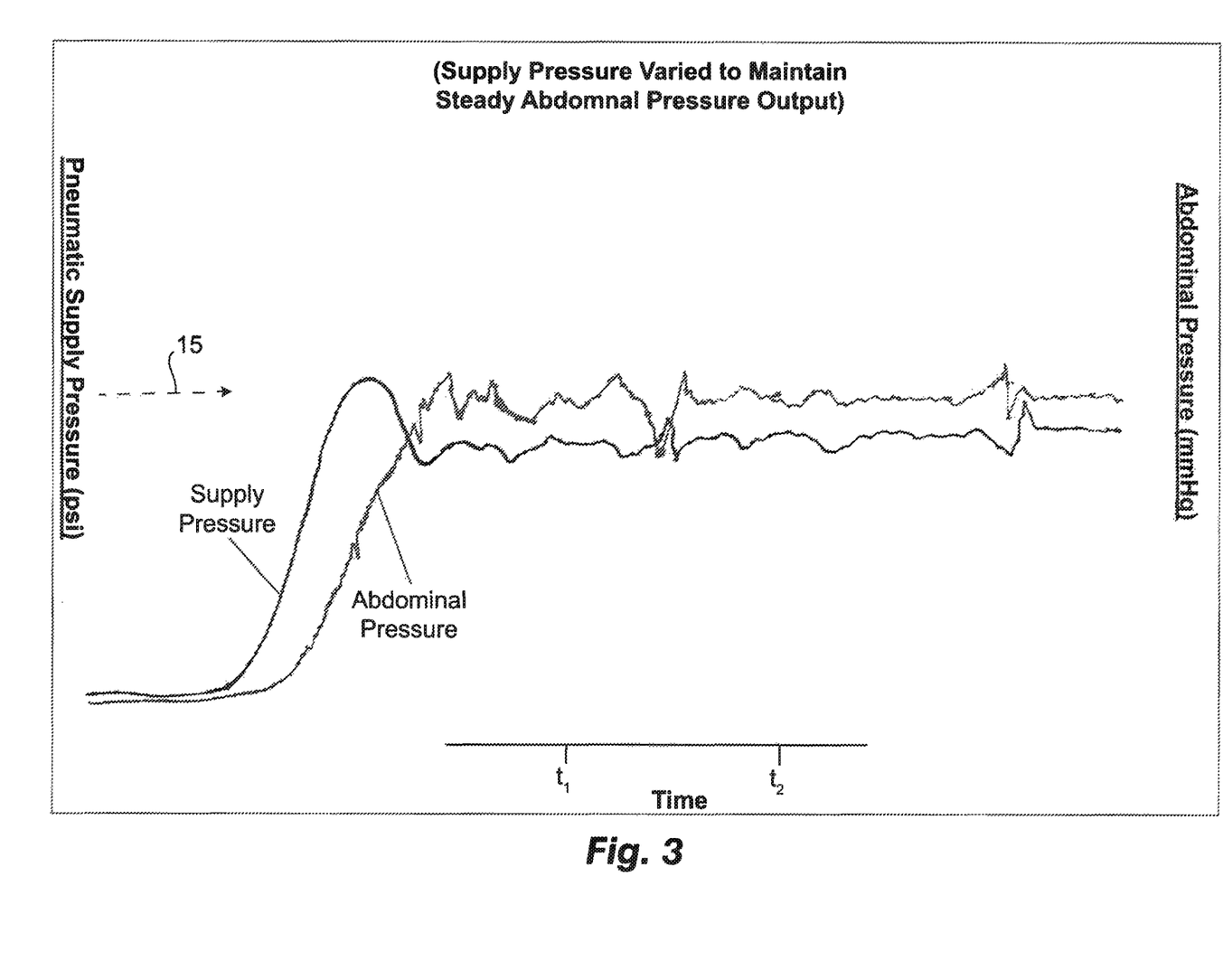
FIG. 3 is a graphical illustration of another simple calibration method wherein pneumatic supply pressure is varied in an effort to maintain steady abdominal cavity pressure output.

Referring to FIG. 3, there is illustrated another example of how a typical, simple calibration process would work. In this method, the design of the loop controller/software is utilized to try to maintain a target abdominal pressure. The system tries to hold a steady output (abdominal pressure) and measures the pneumatic power (supply pressure) required to create that output value. For example, the control software might try to hold abdominal pressure at 15 mmHg and the loop controller will vary the supply pressure according to its software algorithms to try to maintain that target. In FIG. 3, the dashed arrow identified by reference numeral 15 represents the abdominal pressure level that the system is targeting during the calibration.

During this process, a calibration could happen at a single point in time. For example, at the abdominal pressure can be measured at time $t_1$. However, this method is susceptible to disturbances resulting from a leakage or an overpressure condition from someone pushing against the abdomen, which can negatively impact the calibration. Therefore, a better method would be to take an average reading of the supply pressure over a time period (e.g., a straight average or filtered average).

For example, an average can be determined during the period of time extending from $t_1$ to $t_2$. This would reduce the risk of an inaccurate calibration due to external disturbances. A benefit of this calibration method over the method illustrated in FIG. 2 is that the system is allowed to control the selected target abdominal pressure. This achieves a more satisfactory clinical result. On the other hand, this calibration method assumes the loop controller is successful at achieving the target abdominal pressure and looks only at the varying supply pressure for the calibration.

Figure 4:
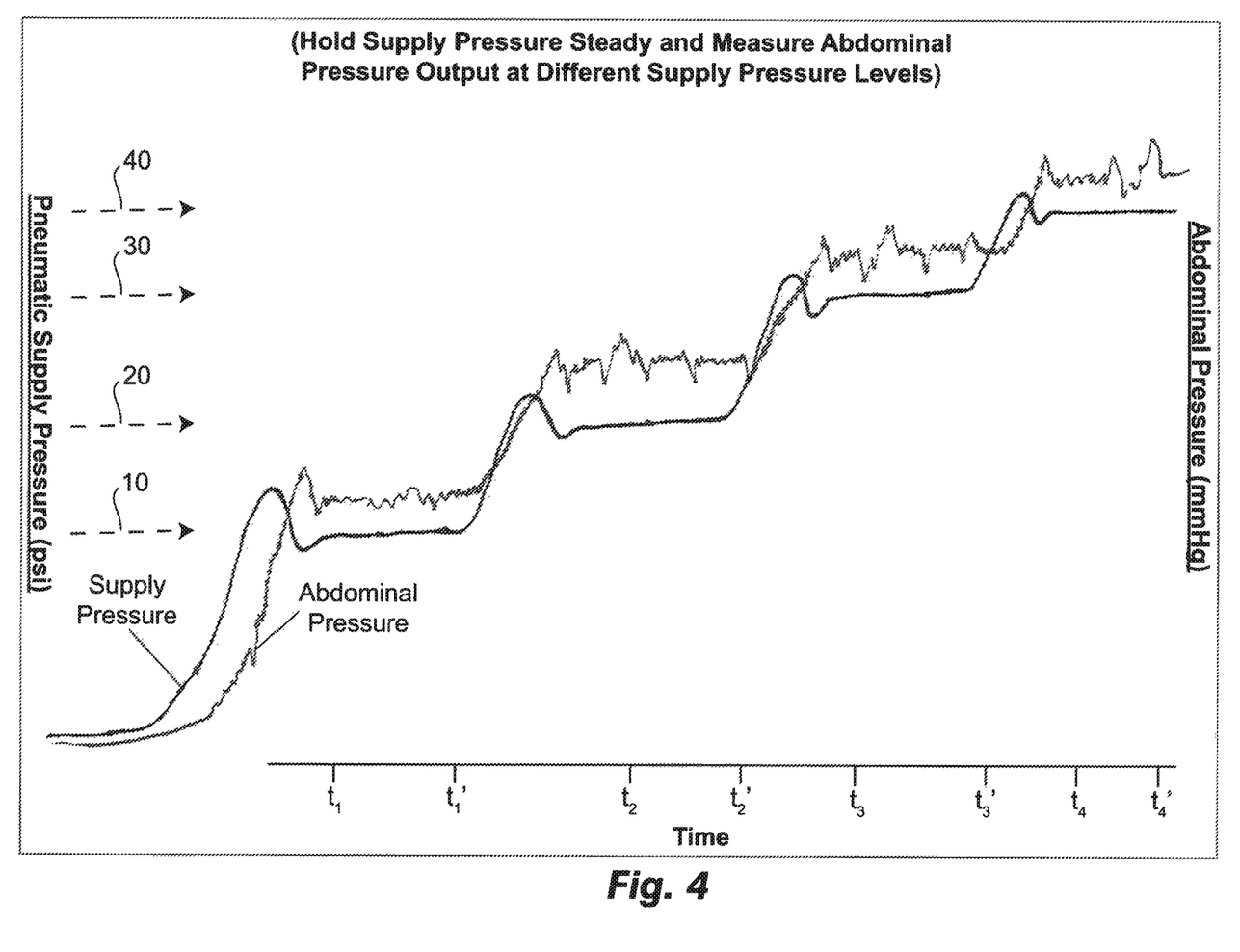
FIG. 4 is a graphical illustration of another basic calibration method, wherein the calibration process repeats in a stepwise manner, with pneumatic supply pressure held steady at four different levels and abdominal cavity pressure output measured at four different levels.

Referring to FIG. 4, there is illustrated another calibration method that is essentially the same as the method illustrated in FIG. 2, but the calibration process is repeated at a series of different steps or pressure levels. In this embodiment, the system holds the supply pressure (pneumatic power) constant at four different levels and measures the output (abdominal pressure) at four different levels.

For example, the software might hold pneumatic supply pressure steady at 10 psi and measure the resultant abdominal pressure, then hold supply pressure steady at 20 psi and measure the abdominal pressure, then at 30 psi, and once again at 40 psi. In FIG. 4, the dotted arrows designated by reference numerals 10, 20, 30 and 40 represent the levels of pneumatic power or supply pressure that the system provides and holds steady during the calibration periods.

During this process, the calibration could happen at individual points in time. For example, abdominal pressure could be measured at times $t_1$, $t_2$, $t_3$ and $t_4$. However, this method is susceptible to disturbances resulting from a leakage or an overpressure condition from someone pushing against the abdomen, which can negatively impact the calibration. Therefore, it would be more preferable to take an average reading over a time period (e.g., a straight average or filtered average). For example, averages could computed during the period extending from $t_1$ to $t_1'$, $t_2$ to $t_2'$, $t_3$ to $t_3'$, and $t_4'$. This would reduce the risk of an inaccurate calibration due to disturbances.

The benefits of this calibration method over the method depicted in FIG. 2, is that this method provides a calibrated behavior over a range of different inputs, giving the system a better overall picture of the behavior of the trocar. On the other hand, this method does not provide control of abdominal pressure, so different trocars will result in different abdominal pressures, which would lead to unsatisfactory clinical results.

Figure 5:
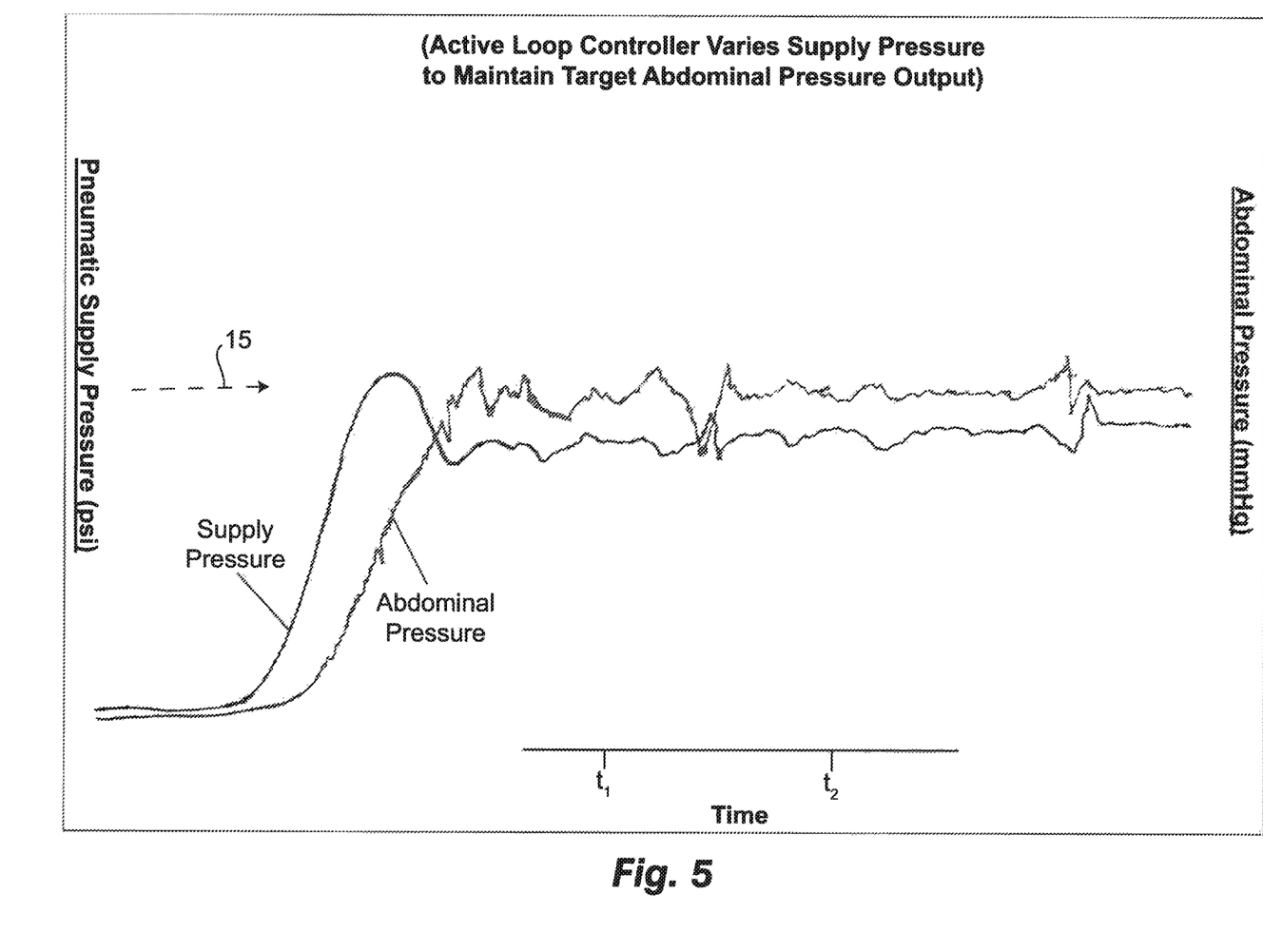
FIG. 5 is a graphical illustration of a calibration method that corresponds to the invention of the subject application, where an active loop controller varies supply pressure to maintain a target abdominal cavity pressure output and calibration is achieved by measuring both input supply pressure and the output achieved.

Referring to FIG. 5, there is illustrated a graphical representation of an embodiment of the novel calibration method of the subject invention. In this method, the loop controller/software is utilized to try to maintain a target abdominal pressure. The red dotted arrow designated by reference numeral 15 represents the abdominal pressure level that the system is targeting during the calibration process.

The system tries to hold a steady output (abdominal pressure) and it measures the pneumatic power (supply pressure) required to create that output value. For example, the system might try to hold abdominal pressure steady at 15 mmHg and the loop controller would vary the supply pressure according to its software algorithms, to try to maintain that target. A calibration could happen at a single point in time, for example at time $t_1$ at which time the abdominal pressure will be taken for the calibration.

The process is susceptible to external influences or disturbances, such as a leakage or an overpressure condition from someone pushing against the abdomen, which can impact the calibration. Therefore, the method can be improved by taking an average of the output pressure and an average of the supply pressure (e.g., a straight average or filtered average) over a period of time.

For example, an average can be taken in the interval between times $t_1$ and $t_2$, in order to reduce the risk of an inaccurate calibration due to disturbances. A benefit of this calibration method over the more typical method of FIG. 2 is that both the supply pressure and the abdominal pressure output are involved in the calibration. Because both the input and the output are averaged over a period of time, this method alleviates the problem in which the system assumes one constant and calibrates a measurement to that value. Instead, using this novel calibration method, the system is associating two sets of measurements.

Figure 6:
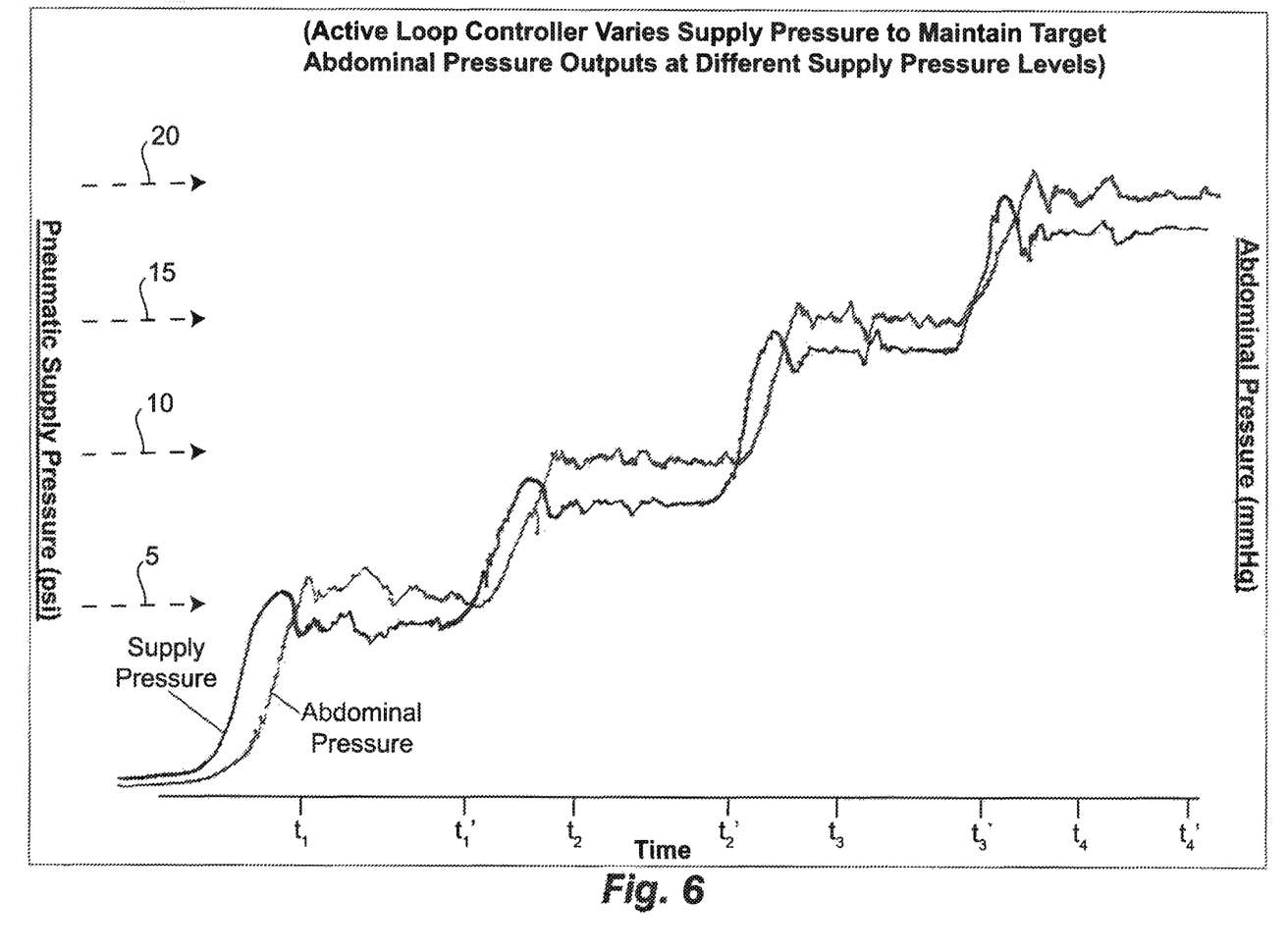
FIG. 6 is a graphical illustration of a calibration method that corresponds to the invention of the subject application, where an active loop controller varies supply pressure to maintain a target abdominal cavity pressure outputs at different steps and calibration is achieved by measuring both input supply pressure and the output achieved at each step.

Referring now to FIG. 6, there is illustrated a graphical representation of another embodiment of the novel calibration method of the subject invention. In this method, the loop controller/software is utilized to try to maintain a target abdominal pressure at four different levels. Moreover, the system tries to hold a steady output (abdominal pressure) and measures the pneumatic power (supply pressure) required to create that output value at each level.

For example, the software might try to hold abdominal pressure steady at 5 mm Hg and the loop controller would vary the supply pressure according to its software algorithms to try to maintain that target, then try to hold abdominal pressure at 10 mm Hg, then at 15 mm Hg and then once again at 20 mm Hg. The arrows in FIG. 6 designated by reference numerals 5, 10, 15 and 20 represent the different abdominal pressure levels that the system is targeting during the calibration process.

The calibration could happen at individual time points. For example, at times $t_1$, $t_2$, $t_3$, and $t_4$, in which the abdominal/supply pressures at each point in time, would be measured for the calibration. In this method, the process is once again susceptible to external influences or disturbances such as a leakage or an overpressure condition, which can have an impact the calibration. Therefore, the method could be improved by calculating an average (e.g., a straight average or filtered average) of the output (abdominal pressure) and an average of the supply pressure (pneumatic power) over a series of time periods, for example, in the period between $t_1$ to $t_1'$, $t_2$ to $t_2'$, $t_3$ to $t_3'$, and $t_4$ to $t_4'$. This would reduce the risk of an inaccurate calibration due to disturbances.

A benefit of this calibration method over the method illustrated in FIG. 4 is that both the supply pressure and the abdominal pressure output are involved in the calibration. Because both the input and the output are averaged over periods of time, this method alleviates the problem in which the system assumes one constant and calibrates a measurement to that value. Instead, using this novel calibration method, the system is associating two sets of measurements. A benefit of this calibration method over the method shown in FIG. 5 is that calibrated behavior is provide over a range of different inputs, giving the system a better overall picture of the behavior of the trocar.

It may be desirable to calibrate the pneumatic performance range of the system to control safety and performance parameters and thresholds which could become particularly important or even required in certain operational modes, such as, for example, for use in pediatric surgery. In addition, calibrating performance to the specific characteristics of the trocar in use will yield a more consistent system behavior that matches the design principles, as opposed to a wide operating range in which different trocars could use up varying portions of that range. By calibrating and applying certain limits and thresholds, each pneumatically sealed trocar will behave with similar bounds, even if they have different baseline characteristics.

By calibrating to the specific performance characteristics of the trocar, it is posited that there can be several additional advantages to the design and manufacturing processes. A calibration process could allow for wider manufacturing tolerances of the trocar which could drive down manufacturing costs. This could allow for a wider design specification range and allow designers and engineers more freedom to design new products and product line extensions. This could enable simpler verification procedures during new product development.

It is furthermore posited that this method could be used for calibration of any number of dynamic systems. For example, water diversion in a plumbed system, dynamic outputs of pneumatic pumps, electrical supply, etc., which could all be "noisy" dynamic systems that require an accurate calibration for its components and subsystems, which could benefit from the calibration method of the subject invention.

While the subject disclosure has been shown and described with reference to preferred embodiments those skilled in the art will readily appreciate that changes and/or modifications may be made thereto without departing from the scope of the subject disclosure.

What is claimed is:

1. A method of calibrating the pneumatic performance range of a system for delivering pneumatic power to a pneumatically sealed trocar, comprising the steps of:

a) supplying pneumatic power to a pneumatically sealed trocar to achieve a desired cavity pressure;
b) measuring the pneumatic power supplied to the pneumatically sealed trocar and cavity pressure over a predetermined time period, as the system attempts to maintain the desired cavity pressure;
c) calculating performance characteristics of the pneumatically sealed trocar based on the measured cavity pressure and pneumatic power values by way of reference to a look-up table with known values, including expected baseline performance values conditional upon corresponding average cavity pressure values and average pneumatic power values; and
d) adjusting the pneumatic power supplied to the pneumatically sealed trocar based upon the calculated performance characteristics of the pneumatically sealed trocar by setting operating limits around the calculated performance characteristics of the trocar.

2. The method of claim 1, further comprising the step of determining an average pneumatic power value and an average cavity pressure value for the time period for calculating the performance characteristics of the trocar.

3. The method of claim 1, further comprising the step of determining a filtered pneumatic power value and a filtered cavity pressure value for the time period for calculating the performance characteristics of the trocar.

4. The method of claim 3, wherein the step of determining a filtered pneumatic power value and a filtered cavity pressure value involves a processing methodology selected from the group consisting of a weighted average, a moving average, a curve-fitting, an additive smoothing, Butterworth filtering, digital filtering, exponential smoothing and low-pass filtering.

5. A method of calibrating the pneumatic performance range of a system for delivering pneumatic power to a pneumatically sealed trocar, comprising the steps of:

a) supplying pneumatic power to a pneumatically sealed trocar to achieve a desired cavity pressure output at a plurality of different output levels;
b) measuring the pneumatic power supplied to the pneumatically sealed trocar and cavity pressure over a predetermined time period at each output level, as the system attempts to maintain the desired cavity pressure at each output level;
c) calculating performance characteristics of the pneumatically sealed trocar based on the measured cavity pressure and pneumatic power values at each output level by way of reference to a look-up table with known values, including expected baseline performance values conditional upon corresponding average cavity pressure values and average pneumatic power values; and
d) adjusting the pneumatic power supplied to the pneumatically sealed trocar based upon the performance characteristics of the pneumatically sealed trocar by setting operating limits around the calculated performance characteristics of the trocar.

6. The method of claim 5, further comprising the step of determining an average pneumatic power value and an average cavity pressure value for the time period at each output level for calculating the performance characteristics of the trocar.

7. The method of claim 5, further comprising the step of determining a filtered pneumatic power value and a filtered cavity pressure value for the time period at each output level for calculating the performance characteristics of the trocar.

8. The method of claim 7, wherein the step of determining a filtered pneumatic power value and a filtered cavity pressure value involves a processing methodology selected from the group consisting of a weighted average, a moving average, a curve-fitting, an additive smoothing, Butterworth filtering, digital filtering, exponential smoothing and low-pass filtering.

\* \* \* \* \*